(12) United States Patent
Plotnikoff

(10) Patent No.: US 8,633,150 B2
(45) Date of Patent: Jan. 21, 2014

(54) METHODS FOR INDUCING SUSTAINED IMMUNE RESPONSE

(75) Inventor: Nicholas P. Plotnikoff, Wilmette, IL (US)

(73) Assignee: TNI Biotech, Inc., Bethesda, MD (US)

( * ) Notice: Subject to any disclaimer, the term of this patent is extended or adjusted under 35 U.S.C. 154(b) by 607 days.

(21) Appl. No.: 10/146,999

(22) Filed: May 16, 2002

(65) Prior Publication Data

US 2003/0148942 A1  Aug. 7, 2003

Related U.S. Application Data

(60) Provisional application No. 60/291,237, filed on May 16, 2001.

(51) Int. Cl.
*A61K 35/12* (2006.01)
(52) U.S. Cl.
USPC ........................................ 514/1.1; 424/277.1
(58) Field of Classification Search
USPC ...................................................... 428/184.1
See application file for complete search history.

(56) References Cited

U.S. PATENT DOCUMENTS

| 4,537,878 | A | | 8/1985 | Plotnikoff | |
|---|---|---|---|---|---|
| 4,757,049 | A | * | 7/1988 | Plotnikoff | 514/17 |
| 4,801,614 | A | | 1/1989 | Plotnikoff | |
| 5,603,933 | A | * | 2/1997 | Dwyer et al. | 424/185.1 |
| 6,017,928 | A | * | 1/2000 | Kempf et al. | 514/314 |

OTHER PUBLICATIONS

Methionine enkephalin: a new cytokine—human studies. Plotnikoff NP, Faith RE, Murgo AJ, Herberman RB, Good RAC: Clin Immunol Immunopathol. Feb. 1997;82(2):93-101.*
Glucocorticoids and the immune function in the human immunodeficiency virus infection: a study in hypercortisolemic and cortisol-resistant patients. Norbiato G, Bevilacqua M, Vago T, Taddei A, Clerici. J Clin Endocrinol Metab. Oct. 1997;82(10):3260-3.*
Dynorphin A toxicity in striatal neurons via an alpha-amino-3-hydroxy-5-methylisoxazole-4-propionate/kainate receptor mechanism. Goody RJ, Martin KM, Goebel SM, Hauser KF. Neuroscience. 2003;116(3):807-16.*
The ontogeny of seizures induced by leucine-enkephalin and beta-endorphin. Snead OC 3rd, Stephens H. Ann Neurol. Jun. 1984;15(6):594-8.*
Human tolerability studies with D-Met2,Pro5-enkephalinamide. Life Sci. 1983;33 Suppl 1:769-72 Foldes J, Torok K, Szekely JI, Borvendeg J, Karczag I, Tolna J, Marosfi S, Varadi A, Gara A, Ronai AZ.*
Abbas et al Cellular and molecular immunolgy, p. 236-237.*
Status of immune-based therapies in HIV infection and AIDS. Fahey JL, Schooley R. Clin Exp Immunol. Apr. 1992;88(1):1-5.*
Discordant Outcomes following Failure of Antiretroviral Therapy Are Associated with Substantial Differences in Human Immunodeficiency Virus-Specific Cellular Immunity DA. Price,1 G Scullard,2 A Oxenius et al. J of Virology, vol. 77, p. 6041. 2003.*
PRNewswire, published Apr. 5, 2001.*
Abbas et al Cellular and molecular immunolgy, p. 236-237, 1991 (amended).*
Zhong et al. (Mar. 1996) "Augmentation of TNF-alpha production, NK cell activity and IL-12 p35 mRNA expression by methionine enkephalin" *Zhongguo Yao Li Xue Bao*, vol. 17, No. 2, abstract.
Yang et al. (Mar. 1992) "Influence of methionine-enkephalin on interleukin-2 production and interleukin-2 receptor expression" *Zhongguo Yao Li Xue Bao*, vol. 13, No. 2, abstract.
Plotnikoff, N.P., et al., "Methionine enkephalin: a new cytokine—human studies", Clin Immunol Immunopathol, Feb. 1997, 82(2):93-101.
Sin, J.I., et al., "Anti-retroviral activity of methionine enkephalin and AZT in a murine cell culture", Int J Immunopharmacol, May 1996, 18(5):305-309.
Specter, S., et al., "Methionine enkephalin used in combination with azidothymidine in murine retrovirus infection", Aids, Drugs of Abuse, and the Neuroimmune Axis, 1996, Freidman et al., editors, Plenum Press, New York, pp. 59-62.
Specter, S., et al., "Methionine enkephalin combined with AZT therapy reduce murine retrovirus-induced disease", Int J Immunopharmacol, Nov. 1994, 16(11):911-917.
Plotnikoff, N., et al., "Methionine-enkephalin shows promise in reducing HIV in blood", Am Fam Physician, Sep. 1989, 40(3):234.
Nagy, J.T., et al., "Activation of the lipoxygenase pathway in the methionine enkephalin induced respiratory burst in human polymorphonuclear leukocytes", Life Sci., 1988, 42(22):2299-2306.
Faith, R.E., et al., "Neuroimmunomodulation with enkephalins: in vitro enhancement of natural killer cell activity in peripheral blood lymphocytes from cancer patients", Nat Immun Cell Growth Regul., 1987, 6(2):88-98.
Plotnikoff, N.P., et al., "Enkephalins and T-cell enhancement in normal volunteers and cancer patients", Ann NY Acad Sci., 1987, 496:608-619.
Wybran, J., et al., "Immunologic properties of methionine-enkephalin, and therapeutic implications in AIDS, ARC, and cancer", Ann NY Acad Sci., 1987, 496:108-114.
Faith, R.E., et al., "Enhancement of host resistance to viral and tumor challenge by treatment with methionine-enkephalin", Ann NY Acad Sci., 1987, 496:137-145.
Nagy, J.T., et al., "Possible correction of defective polymorphonuclear cell functions in type-2 diabetes mellitus by met-enkephalin", Ann NY Acad Sci., 1987, 496:166-169.
Plotnikoff, N.P., et al., "Methionine enkephalin: immunomodulator in normal volunteers (in vivo)", Psychopharmacol Bull., 1986, 22(4):1097-1100.
Murgo, A.J., et al., "Effect of methionine-enkephalin plus ZnCl2 on active T cell rosettes", Neuropeptides, Feb. 1985, 5(4-6):367-370.
Plotnikoff, N.P., et al., "Enkephalins: immunomodulators", Fed Proc., Jan. 1985, 44(1 Pt 1):118-122.
Plotnikoff, N.P., et al., "Neuroimmunomodulation with enkephalins: effects on thymus and spleen weights in mice", Clin Immunol Immunopathol., Jul. 1984, 32(1):52-56.
Faith, R.E., et al., "Neuroimmunomodulation with enkephalins: enhancement of human natural killer (NK) cell activity in vitro", Clin Immunol Immunopathol., Jun. 1984, 31(3):412-418.

(Continued)

*Primary Examiner* — Lei Yao
(74) *Attorney, Agent, or Firm* — Birch, Stewart, Kolasch & Birch, LLP

(57) ABSTRACT

A method for promoting a sustained increased level of T-cell production in immunocompromised subjects in which method enkephalin peptides are administered according to an intermittent dose schedule. In particular, the method involves treatment of immunocompromised patients which includes the administration of enkephalin, either alone or in conjunction with other therapies, in an initial dosage regimen, with periodic booster dosages of enkephalin as necessary to maintain sustained immune system response.

8 Claims, No Drawings

(56) References Cited

OTHER PUBLICATIONS

Miller, G.C., et al., "Enkephalins—enhancement of active T-cell rosettes from normal volunteers", Clin Immunol Immunopathol., Apr. 1984, 31(1):132-137.

Faith, R.E., et al., "Effects of opiates and neuropeptides on immune functions", NIDA Res Monogr., 1984, 54:300-311.

Miller, G.C., et al., "Enkephalins—enhancement of active T-cell rosettes from lymphomal patients", Clin Immunol Immunopathol., Mar. 1983, 26(3):446-451.

Plotnikoff, N.P., et al., "Enkephalins as immunomodulators", Int J. Immunopharmacol, 1983, 5(5):437-441.

Foldes, J., et al., "Human Tolerability Studies with D-Met, Pro-enkephalinamide", Life Sciences, 1983, 33(Supp I):769-772.

Smith, J.P., et al., "Treatment of advanced pancreatic cancer with opiod growth factor: phase I", Anticancer Drugs, Mar. 2004, 15(3):203-209.

Von Graffenried, B., et al., "Effects of the synthetic enkephalin analogue FK 33-824 in man", Nature, Apr. 20, 1978, 272:729-730.

Office action issued in related Russian patent application No. 2003136161 on Feb. 15, 2005, with English-language translation, 15 pages total.

Office action issued in related Russian patent application No. 2003136161 on Apr. 19, 2006, with English-language translation, 6 pages total.

Ogawa, K., et al., "Suppression of cellular immunity by surgical stress", Surgery, Mar. 2000, 127(3):329-336, abstract.

\* cited by examiner

SEQUENCE LISTING

<160> NUMBER OF SEQ ID NOS: 18

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is Met or Leu.

<400> SEQUENCE: 1

Tyr Gly Gly Phe Xaa
1               5

<210> SEQ ID NO 2
<211> LENGTH: 16
<212> TYPE: PRT
<213> ORGANISM: Homo sapiens

<400> SEQUENCE: 2

Tyr Gly Gly Phe Met Thr Ser Glu Lys Ser Gln Thr Pro Leu Val Thr
1               5                   10                  15

<210> SEQ ID NO 3
<211> LENGTH: 17
<212> TYPE: PRT
<213> ORGANISM: Homo sapiens

<400> SEQUENCE: 3

Tyr Gly Gly Phe Met Thr Ser Glu Lys Ser Gln Thr Pro Leu Val Thr
1               5                   10                  15

Leu

<210> SEQ ID NO 4
<211> LENGTH: 31
<212> TYPE: PRT
<213> ORGANISM: Homo sapiens

<400> SEQUENCE: 4

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 5
<211> LENGTH: 5
<212> TYPE: PRT
<213> ORGANISM: Homo sapiens

<400> SEQUENCE: 5

Tyr Gly Gly Phe Leu
1               5

<210> SEQ ID NO 6
<211> LENGTH: 5
<212> TYPE: PRT
<213> ORGANISM: Homo sapiens

<400> SEQUENCE: 6

Tyr Gly Gly Phe Met
1               5

```
<210> SEQ ID NO 7
<211> LENGTH: 7
<212> TYPE: PRT
<213> ORGANISM: Homo sapiens

<400> SEQUENCE: 7

Tyr Gly Gly Phe Met Arg Gly
1               5

<210> SEQ ID NO 8
<211> LENGTH: 8
<212> TYPE: PRT
<213> ORGANISM: Homo sapiens

<400> SEQUENCE: 8

Tyr Gly Gly Phe Met Arg Gly Leu
1               5

<210> SEQ ID NO 9
<211> LENGTH: 25
<212> TYPE: PRT
<213> ORGANISM: Bovine

<400> SEQUENCE: 9

Tyr Gly Gly Phe Met Arg Arg Val Gly Arg Pro Glu Trp Trp Met Asp
1               5                   10                  15

Tyr Gln Lys Arg Tyr Gly Gly Phe Leu
            20                  25

<210> SEQ ID NO 10
<211> LENGTH: 8
<212> TYPE: PRT
<213> ORGANISM: Homo sapiens

<400> SEQUENCE: 10

Tyr Gly Gly Phe Leu Arg Arg Ile
1               5

<210> SEQ ID NO 11
<211> LENGTH: 17
<212> TYPE: PRT
<213> ORGANISM: Porcine

<400> SEQUENCE: 11

Tyr Gly Gly Phe Leu Arg Arg Ile Arg Pro Lys Leu Lys Trp Asp Asn
1               5                   10                  15

Gln

<210> SEQ ID NO 12
<211> LENGTH: 13
<212> TYPE: PRT
<213> ORGANISM: Porcine

<400> SEQUENCE: 12

Tyr Gly Gly Phe Leu Arg Arg Gln Phe Lys Val Val Thr
1               5                   10

<210> SEQ ID NO 13
<211> LENGTH: 10
<212> TYPE: PRT
<213> ORGANISM: Homo sapiens

<400> SEQUENCE: 13

Tyr Gly Gly Phe Leu Arg Lys Tyr Pro Lys
1               5                   10
```

```
<210> SEQ ID NO 14
<211> LENGTH: 9
<212> TYPE: PRT
<213> ORGANISM: Homo sapiens

<400> SEQUENCE: 14

Tyr Gly Gly Phe Leu Arg Lys Tyr Pro
1               5

<210> SEQ ID NO 15
<211> LENGTH: 29
<212> TYPE: PRT
<213> ORGANISM: Porcine

<400> SEQUENCE: 15

Tyr Gly Gly Phe Leu Arg Arg Gln Phe Lys Val Val Thr Arg Ser Gln
1               5                   10                  15

Glu Asp Pro Asn Ala Tyr Tyr Glu Glu Leu Phe Asp Val
            20                  25

<210> SEQ ID NO 16
<211> LENGTH: 7
<212> TYPE: PRT
<213> ORGANISM: Homo sapiens

<400> SEQUENCE: 16

Tyr Pro Phe Pro Gly Pro Ile
1               5

<210> SEQ ID NO 17
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Ala at position 2 is D-ala.
<220> FEATURE:
<221> NAME/KEY: MISC_FEATURE
<222> LOCATION: (7)..(7)
<223> OTHER INFORMATION: Ser is linked covalently to amino group.

<400> SEQUENCE: 17

Tyr Ala Phe Gly Tyr Pro Ser
1               5

<210> SEQ ID NO 18
<211> LENGTH: 2
<212> TYPE: PRT
<213> ORGANISM: Homo sapiens

<400> SEQUENCE: 18

Tyr Arg
1
```

METHODS FOR INDUCING SUSTAINED IMMUNE RESPONSE

FIELD OF THE INVENTION

The present invention relates to methods of stimulating and promoting a sustained natural immune system response, resulting in increased resistance and inhibition of infectious agents, including viruses, bacteria, fungi and parasites, and other immunodeficiency-related ailments. More specifically, the invention relates to an intermittent dose schedule for promoting a sustained increased level of T-cell production (cytotoxic T cells).

BACKGROUND OF THE INVENTION

The immune system protects the body against infectious agents, including bacteria, viruses, fungi, and parasites. In addition, the immune system protects against cancer, as well as disease states that result from immune imbalance, opportunistic infections, and autoimmune disorders (Penney, U.S. Pat. No. 5,980,913). Stimulation of the immune system by pharmaceuticals is an important approach to the prevention and treatment of agents that cause immune suppressed states.

The response by the immune system to an immunogen may be depressed as a consequence of certain diseases or pathological conditions. For example, patients infected with the human immunodeficiency virus (HIV-1) may develop acquired immune deficiency syndrome (AIDS) or AIDS related complex (ARC), and thus have depressed immune responses. This patient class is more susceptible to pathological infections or malignancies against which a normal immune system would have otherwise provided sufficient protection. Other such immunocompromised individuals include patients with cancer, or undergoing x-ray, surgery, or chemotherapy treatment.

Current treatments used to prevent the development of immunodeficiency in individuals with viral infections, HIV for example, usually involve administration of compounds that inhibit viral DNA synthesis thereby slowing onset of viral-related immunosuppression. Treatments for HIV-infected patients often involves administration of compounds such as, for example, 3'-azido-3'-deoxythymidine (AZT), 2',3'-dideoxycytidine (DDC) and 2',3'-dideoxyinosine (DDI), zidovudine, didanosine, zalcitabine, stavudine, and viramune. More recent treatments against HIV include administration of protease inhibitors such as, for example, saquinovir, nefinavir, ritonavir, indinavir, and others. Cytokine therapy is also used in the treatment of AIDS patients, with research groups having demonstrated efficacy of interleukin-2 (IL2) in elevating the CD4 T-cell subset in HIV positive patients (Kovacs, et al., *N. Engl. J. Med.*, 1996; 335: 1350-1356). Reports have detailed that IL2 can also increase CD8 T-cell count (Schmitz, et al., *Science*, 1999; 283: 857-860). Unfortunately, the use of IL2 is normally accompanied by major toxicity (Davey, et al., *JAMA*, 2000; 284: 183-189). Nevertheless, given the potential promise of these therapies directed toward anti-retroviral effects, none have proven to be totally effective in treating or preventing development of AIDS. In addition, many of these compounds cause adverse side effects including low platelet count, diarrhea, nausea, renal toxicity, and bone marrow cytopenia (Kempf, et al., U.S. Pat. No. 6,017,928; Lai, et al., U.S. Pat. No. 6,093,743). Numerous clinical studies with methionine enkephalin (met-enkephalin) in normal volunteers, HIV positive, and cancer patients showed no major toxicity (Plotnikoff, et al, *Clin. Immun. Immunopath.*, 1997). However, the measured half-life of met-enkephalin in plasma is approximately 2 minutes (Bihari, et al., *Seventh Int. Conf. On AIDS,* 1991). Thus, there exists a need in the art for improved methods of stimulating a sustained immune system response in patients in need of such treatment, such as patients include those with compromised immune system responses (e.g. AIDS), or the potential to develop compromised immune system responses (e.g. HIV-infected patients).

SUMMARY OF THE INVENTION

All cited patents, patent applications and references are hereby incorporated by reference in their entirety.

Recent studies of met-enkephalin indicated that met-enkephalin activated gene transcription of IL2 (Wybran, et al., from *Some Immunological Effects of Methionine-Enkephalin In Man: Potential Therapeutical Use Leukocytes and Host Defense.* 205-212, Alan R. Liss, Inc. 1986) and gamma interferon (Brown, et al., *Immunology,* 1986; 103: 19-26) and IL 12, (Zhong, et al., Augmentation of TNF-alpha Production, NK cell activity and IL-12 p35 mRNA Expression by Metliaonine Enkephalin, 1996;17(2): 182-5) AIDS patients have a deficiency of IL2, and gamma interferon (Fauci, et al., *Science,* 1993; 262: 1011-1018). Recently HIV positives have shown a deficiency of met-enkephalin (Valentine, et al., *FASEB J.,* 1988; 2(5): 4518; Chao, Thesis, University of Illinois College of Pharmacy 1993). All of the above cytokines are derived from prohormones in T helper cells (Plotnikoff, et al., *Clin. Immun. Immunopath.,* 1997; 82(2): 93-101). Immune suppression is, in part, a consequence of cyctokine deficiency (Fauci, et al., *Science,* 1993; 262: 1011-1018).

Based on the above, however, there would be no expectation by one of skill in the art that the active agents of the present invention could be used in methods of treatment useful in producing a sustained immune response in a patient comprising administering the active agents on an intermittent dosage schedule to a patient in need of such treatment.

The present invention is based on the surprising discovery that a regular dosing schedule of met-enkephalin is effective in promoting a sustained cell increase in immune system response including sustained cell levels, in a patient for at least one month after cessation of the dosing.

The present invention provides, inter alia, for methods of treatment useful for inducing a sustained immune system response in an immunocompromised patient in need of such treatment wherein the method comprises administering to the patient an effective amount of an enkephalin peptide, either alone, combined, or in further combination with other compounds useful for increasing immune system response, including vaccines. In this context, "immunocompromised" refers to any reduction in T-cell number or function.

The present invention also provides, inter alia, for methods of treatment useful for inducing a sustained immune system response in an HIV-infected patient, wherein the method comprises administering to the HIV-infected patient an effective amount of an enkephalin peptide, either alone, combined, or in further combination with other compounds useful for slowing the progression of HIV proliferation or HIV-associated infections, including reverse transcriptase inhibitors such as 3'-azido-3'-deoxythymidine (AZT), 2',3'-dideoxycytidine (DDC) and 2',3'-dideoxyinosine (DDI), zidovudine, didanosine, zalcitabine, stavudine, and viramune; protease inhibitors such as saquinovir, nefinavir, ritonavir, and indinavir; cytokines such as G-CSF, IL-11, IL-12, IL-2; and gamma interferon and antibiotics or other drugs used for the treatment or prevention of infections in HIV-infected patients.

DETAILED DESCRIPTION OF THE PREFERRED EMBODIMENTS

Definitions

Unless otherwise indicated, the term "active agents" as used herein refers to the group of compounds comprising the class of enkephalin peptides.

Unless otherwise indicated, the term "enkephalin" or "enkephalin peptides" includes any compound that falls into the general category of opioid peptide molecules, including compounds having the following peptide structure at one terminus:
Tyr-Gly-Gly-Phe-R(SEQ. ID. NO. 1)
where R is either Met or Leu. Exemplary enkephalin peptides are shown in Table 1.

106, to Wilkinson, issued Mar. 3, 1981; U.S. Pat. No. 4,213,968, to Kastin et al., issued Jul. 22, 1980; U.S. Pat. No. 4,198,398, to Hudson et al., issued Apr. 15, 1980; U.S. Pat. No. 4,127,534, to Coy et al., issued Nov. 28, 1978; U.S. Pat. No. 4,092,304, to Jones, Jr. et al., issued May 30, 1978; U.S. Pat. No. 4,028,319, to Jones, Jr. et al., issued Jun. 7, 1977; J. Chang et al., "Opiate Receptor Affinities and Behavioral Effects of Enkephalin: Structure Activity Relationship of Ten Synthetic Peptide Analogues," 18 Life Sci. 1473-1482 (1976); G. A. Gacel et al., "Synthesis, Biochemical and Pharmacological Properties of BUBUC, a Highly Selective and Systematically Active Agonist for In Vivo Studies of Delta-Opioid Receptors", 11 Peptides 983-988 (1990); and B. P. Roques, "Peptidomimetics as Receptor Agonists or Peptidase

TABLE 1

Opioid peptides and their precursors and structures

| Precursors | Peptides | Structures |
|---|---|---|
| Pro-Opiomelanocortin (PCMC) | α-Endorphin | Tyr-Gly-Gly-Phe-Met-Thr-Ser-Glu-Lys-Ser-Gln-Thr-Pro-Leu-Val-Thr (SEQ. ID. NO. 2) |
| | λ-Endorphin | Tyr-Gly-Gly-Phe-Met-Thr-Ser-Glu-Lys-Ser-Gln-Thr-Pro-Leu-Val-Thr-Leu (SEQ. ID. NO. 3) |
| | β-Endorphin (human) | Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu (SEQ. ID. NO. 4) |
| Proenkephalin A | Leu-enkephain | Tyr-Gly-Gly-Phe-Leu (SEQ. ID. NO. 5) |
| | Met-enkephailin | Tyr-Gly-Gly-Phe-Met (SEQ. ID. NO. 6) |
| | Heptapeptide | Tyr-Gly-Gly-Phe-Met-Arg-Gly (SEQ. ID. NO. 7) |
| | Octapeptide | Tyr-Gly-Gly-Phe-Met-Arg-Gly-Leu (SEQ. ID. NO. 8) |
| | Peptide E (bovine) | Tyr-Gly-Gly-Phe-Met-Arg-Arg-Val-Gly-Arg-Pro-Glu-Trp-Trp-Met-Asp-Tyr-Gln-Lys-Arg-Tyr-Gly-Gly-Phe-Leu (SEQ. ID. NO. 9) |
| Prodynorphin (Proenkephalin B) | Dynorphin A(1-8) | Tyr-Gly-Gly-Phe-Leu-Arg-Arg-Ile (SEQ. ID. NO. 10) |
| | Dynorphin A(1-17) (porcine) | Tyr-Gly-Gly-Phe-Leu-Arg-Arg-Ile-Arg-Pro-Lys-Leu-Lys-Trp-Asp-Asn-Gln (SEQ. ID. NO. 11) |
| | Dynorphin B(1-13) (porcine) | Tyr-Gly-Gly-Phe-Leu-Arg-Arg-Gln-Phe-Lys-Val-Val-Thr (SEQ. ID. NO. 12) |
| | α-Neo-endorphin | Tyr-Gly-Gly-Phe-Leu-Arg-Lys-Tyr-Pro-Lys (SEQ. ID. NO. 13) |
| | β-Neo-endorphoin | Tyr-Gly-Gly-Phe-Leu-Arg-Lys-Tyr-Pro (SEQ. ID. NO. 14) |
| | New dynorphin (ieumorphin) (porcine) | Tyr-Gly-Gly-Phe-Leu-Arg-Arg-Gln-Phe-Lys-Val-Val-Thr-Arg-Ser-Gln-Glu-Asp-Pro-Asn-Ala-Tyr-Tyr-Glu-Glu-Leu-Phe-Asp-Val (SEQ. ID. NO. 15) |
| Others | β-Casomorphin | Tyr-Pro-Phe-Pro-Gly-Pro-Ile (SEQ. ID. NO. 16) |
| | Dermorphin | Tyr-d-Ala-Phe-Gly-Tyr-Pro-Ser-$NH_2$ (SEQ. ID. NO. 17) |
| | Kyotorphin | Tyr-Arg (SEQ. ID. NO. 18) |

Enkephalin analogues also fall within the scope of this invention, and are described in the following references which are incorporated by reference: U.S. Pat. No. 4,468,383, to Rodbard et al., issued Aug. 28, 1984; U.S. Pat. No. 4,371,463, to Pert et al., issued Feb. 1, 1983; U.S. Pat. No. 4,261,883, to Smolarsky, issued Apr. 14, 1981; U.S. Pat. No. 4,254, Inhibitors: A Structural Approach in the Field of Enkephalins, ANP and CCK", 32 Biopolymers 407-410 (1992).

As used herein, the term "sustained immune system response" is taken to mean maintaining in a patient an increase from the baseline of serum levels of cells and molecules associated with the immune system, including T-cells such as CD3, CD4, CD8, CD56, CD 25, and CD38 and molecules such as the interleukins and interferons.

As used herein, the term "baseline" or "base level response" is taken to mean the serum levels in a patient before administration of active agent of cells and molecules associated with the immune system, including T-cells such as CD3, CD4, CD8, CD56, CD 25, and CD38 and molecules such as the interleukins and interferons.

The phrase "intermittent dose schedule" of enkephalin peptides as used herein refers to an initial routine of repeated administration of a enkephalin peptides, ranging from a daily to a weekly basis for some defined period of time (or, alternatively, a compound that promotes in vivo production of enkephalin peptides for some defined period of time) (collectively referred to as an "initial dosage regimen"), followed by a period of time when such administration is discontinued. Additional enkephalin peptides (or compounds that promote in vivo production of enkephalin peptides) are administered thereafter on an intermittent basis.

Exemplary intermittent dose schedules include, but are not limited to, administration of enkephalin peptides from one to five times a week over the course of a 12 week period, then discontinued for a period of time ranging from 4 to 24 weeks. Thereafter, based on some defined criteria, booster doses are given, up to 5 times a week for 1 to 4 weeks. Other examples of intermittent dose schedules that fall within the scope of this invention include administration of enkephalin peptides from 1 to 5 times a week over 4 weeks, then discontinued for a period of time ranging from 4 to 16 weeks. Thereafter, booster doses are given, up to 5 times a week for 1 to 4 weeks, depending on the level of sustained response measured. Other intermittent schedules may also be utilized.

As used herein, the term "HIV" includes all variants and types of HIV-1, HIV-2, and other synonymous retroviruses, such as human T-lymphotropic virus type III (HTLV-III) and lymphadenopathy associated virus (LAV-1 and LAV-2).

As used herein, the term "AIDS" refers to acquired immune deficiency syndrome, AIDS-related complex (ARC), and decreased lymphocyte numbers in HIV-infected individuals.

As used herein, the term "treating or preventing AIDS" includes preventing or decreasing the immunosuppression caused by AIDS, for example, by decreasing HIV levels in the patient's peripheral blood lymphocytes, or by increasing lymphocyte numbers; replenishing the bone marrow; increasing survival of HIV-infected patients; as well as preventing or decreasing the associated symptoms, disorders, and infections associated with HIV infection, including but not limited to susceptibility to pathogenic and opportunistic organisms and infections, anemia, thrombocytopenia, and lymphopenia.

As used herein, the term "opportunistic infection" refers to infections with an organism that would not normally be pathologic in patients with properly functioning immune systems.

Many of the peptides contemplated in the instant invention are commercially available, but alternatively may be synthesized by any conventional method, including, but not limited to, those set forth in J. M. Stewart and J. D. Young, *Solid Phase Peptide Synthesis,* 2nd ed., Pierce Chemical Co., Rockford, Ill. (1984) and J. Meienhofer, *Hormonal Proteins and Peptides,* Vol. 2, Academic Press, New York, (1973) for solid phase synthesis and E. Schroder and K. Lubke, *The Peptides,* Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

The peptides can synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Alternatively, the peptides may be produced via conventional molecular biological methods.

Description

In one embodiment of the invention an effective amount of active agent is administered to a patient once a week over the course of a 12 week period, then stopped. Measurement of the patient's immune response (T-cell counts) is made from 4 to 16 weeks after cessation of the initial dosing, and compared with both the base level response and response levels measured at the end of the dosing schedule. Thereafter, booster doses are given, as needed, up to 5 times a week for 1 to 4 weeks.

In other embodiments of the invention an effective amount of active agent is administered to a patient from 1 to 5 times a week over the course of a 4 week period, then stopped. Measurement of the patients' immune response (T-cell counts) is made from 4 to 16 weeks after cessation of the initial dosing. Thereafter, booster doses are given, as needed, up to 5 times a week for 1 to 4 weeks, depending on the level of sustained response measured. Other intermittent schedules may also be utilized.

In one aspect of the present invention methods for treating or preventing AIDS in an HIV-infected patient, comprising administering to an HIV-infected patient an amount effective to treat or prevent AIDS of at least one compound selected from the group of active agents, alone, in combination with each other, or in combination with other compounds that are beneficial for treating or preventing AIDS in HIV-infected individuals, including but not limited to reverse transcriptase inhibitors including but not limited to 3'-azido-3'-deoxythymidine (AZT), 2',3'-dideoxycytidine (DDC) and 2',3'-dideoxyinosine (DDI), zidovudine, didanosine, zalcitabine, stavudine, and viramune; protease inhibitors such as saquinovir, nefinavir, ritonavir, and indinavir; cytokines such as G-CSF, IL-11, IL-12 and IL-2 and erythropoietin; and antibiotics or other drugs used for the treatment or prevention of infections in HIV-infected patients or vaccines.

For use in treating or preventing onset of AIDS in an HIV-infected individual, the active agents may be administered by any suitable route, but are preferably administered either orally, parentally, by inhalation spray, transdermally, intravenously, rectally, intra-arterially, nasally, eye-drops, buccal patch or topically in dosage unit formulations containing conventional pharmaceutically acceptable carriers, adjuvants, and vehicles. The term parenteral as used herein includes subcutaneous, intramuscular, intravenously, intra-arterially, or intratendinous.

The active agent may also be administered directly to the individual in a pharmaceutically suitable vehicle, for example, a solution of 5% DMSO or 10% ethanol in saline. In a preferred embodiment, multiple administrations of the active agents are made over the period of time encompassing effective treatment.

A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; crystalloid and viscous instillates; absorbable and/or biodegradable mechanical barriers; and polymeric delivery materials, such as polyethylene oxide/polypropylene oxide block copolymers (e.g. poloxamers), poly-orthoesters, cross-linked polyvinyl alcohol, polyanhydrides, polymethacrylate and polymethacryladmide hydrogels, anionic carbohydrate polymers, polyethylene glycol, etc. Useful delivery systems are well known in the art and are described in, e.g., U.S. Pat. No. 4,937,254, the entire disclosure of which is hereby incorporated by reference.

The active agents may be made up in a liquid form (e.g., solutions, suspensions, or emulsions), and may be subjected to conventional pharmaceutical operations such as sterilization and/or may contain conventional pharmaceutically acceptable adjuvants, such as stabilizers, wetting agents, emulsifiers, preservatives, cosolvents, suspending agents, viscosity enhancing agents, ionic strength and osmolality adjustors and other excipients in addition to buffering agents. Suitable water-soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the active agent is ordinarily combined with one or more pharmaceutically acceptable adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers including phosphate buffered saline. Other adjuvants and modes of administration are well known in the pharmaceutical art. The carrier or diluent may include time delay material, such as glyceryl monostearate or glyceryl distearate alone or with a wax, or other materials well known in the art.

The dosage regimen of the active agents for inducing sustained immune system response in HIV-infected patients is based on a variety of factors, including the age, weight, sex, medical condition of the individual, the severity of the condition, the route of administration, and the particular active agent to be administered. Thus, the dosage regimen may vary widely, but can be determined routinely by a physician using standard methods. Dosage levels of the order of between $10^{-14}$ μg/Kg to 30,000 μg/Kg of the active agents per body weight may be used for all methods of use disclosed herein. Preferred dosage levels range from 1 μg/Kg to 250 μg/Kg in the intermittent dose schedules. In a preferred embodiment, dosages during the initial dosage regimen are 20 μg/Kg bodyweight of the subject and intermittent dosages after such initial dosage regimen range from 20 to 100 μg/Kg bodyweight.

The efficacy of the dosing schedules are determined by methods that measure indications such as decreases in HIV levels in the patient's peripheral blood lymphocytes, (viral load), anemia, thrombocytopenia, and lymphopenia; and increased CD4+, CD8+, CD3+, and CD56+ cell counts, lymphocyte numbers, antibody titer, resistance to pathogenic and opportunistic infections, and survival of HIV-infected patients.

The active agents of the present invention may also be administered in a further stabilized form, such as, for example, associated with polyethylene glycol or as a fusion protein, or other forms known in the art.

AIDS, surgery patients and cancer patients have been shown to have elevated cortisol levels resulting in suppression of cytokine production, such as IL2 and gamma interferon. Such suppression of cytokine production contributed to the suppression of the immune system. Cortisol, in particular, is believed to have inhibitory effect on gene transcription of IL2, and down-regulates cytotoxic cells and NK lymphocytes. See, e.g., K. Ogawa et al., "Suppression of Cellular Immunity by Surgical Stress," *Surgery*, 127(3): 329-36 (March, 2000); "Suppressant Effects of Cortisol," Goodman and Gilmans, *The Pharmacological Basis of Therapeutics*, Pergamon Press, New York (8$^{th}$ Ed. 1990). Cortisol also produces fatigue and weakness in AIDS patients. The studies reported in the examples demonstrate that an intermittent dosage regimen of met-enkephalin reverses HIV-induced immune suppression resulting in increased IL2 levels and T cells and would be expected to reverse such immune suppression induced by a common pathway—cortisol—as seen in AIDS, surgery, cancer, and other patients.

The present invention may be better understood with reference to the accompanying examples that are intended for purposes of illustration only and should not be construed to limit the scope of the invention.

EXAMPLE 1

In vivo Administration of Met-Enkephalin as a 'Therapeutic Vaccine'

An original 12 week double blind study designed to measure the effects of a regular dosing schedule of met-enkephalin on cytotoxic T cells levels in HIV-infected patients was undertaken. Dosages for each patient varied according to group: (1) 60 μg/Kg; (2) 125 μg/Kg and (3) placebo. The patients were administered either active agent (met-enkephalin) or placebo (normal saline; control group) once a week for twelve weeks by means of intravenous infusions. At the eight and twelve week mark, samples from each patient were taken in order to measure levels of T-cells. At twelve weeks the infusions were stopped. Measurement of T-cell counts were again recorded 4 weeks after stopping the infusions (16 week time point). The results show sustained response levels of cytotoxic T cells a month after the last dosing of met-enkephalin.

TABLE II

Immunological Values One Month After Last N-Saline Infusion

|  | BASELINE | ONE MONTH | DIFFERENCE |
|---|---|---|---|
| CD3 (6/8) | 1260 ± 136(1) | 976 ± 103* | −284 |
| CD4 (6/8) | 383 ± 37 | 304 ± 37* | −79 |
| CD8 (5/8) | 914 ± 153 | 668 ± 104* | −246 |
| CD56 (7/8) | 22 ± 6 | 80 ± 18* | +58 |
| CD25 (5/8) (IL2 Receptor) | 45 ± 8 | 90 ± 17* | +45 |
| CD38 (7/8) | 220 ± 8 | 505 ± 84 | +285 |

CD3 *P = 0.01
CD4 *P = 0.001
CD8 *P = 0.02
CD56 *P = 0.01
CD25 *P = 0.02
CD38 *P = 0.01
(1)Mean cell numbers is. e. per cu.mm.
(N/8) Number of patients with cell counts above (or below) baseline

TABLE III

IMMUNOLOGICAL VALUES ONE MONTH AFTER LAST N-METHIONINE ENKEPHALIN INFUSION

|  | BASELINE | ONE MONTH | DIFFERENCE |
|---|---|---|---|
| CD3 (9/12) | 1003 ± 81(1) | 1183 ± 116* | +180 |
| CD4 (7/12) | 314 ± 39 | 351 ± 37* | +37 |
| CD8 (9/12) | 659 ± 64 | 787 ± 79* | +128 |
| CD56 (11/12) | 22 ± 6 | 137 ± 6* | +115 |
| CD25 (10/12) (IL-2 receptor) | 58 ± 12 | 145 ± 62* | +87 |
| CD38 (9/12) | 320 ± 79 | 636 ± 103* | +316 |

(1)Mean cell numbers of cells ± s.e. per cu.mm
CD3 *P = 0.04
CD4 *P = 0.01
CD8 *P = 0.001
CD56 *P = 0.001
CD25 *P = 0.09
CD38 *P = 0.05
(N/12) Number of patients with cell counts above baseline Summary of Results:

Cytotoxic T cells (including CD3, CD4 and CD8 cells) were found to be elevated compared to baseline values one month after the last dosing of methionine enkephalin (8-12 weeks infusion). In sharp contrast the placebo treated control group had a progressive decrease of the same cells over the 16 week study. The results indicate that treatment with met-enkephalin increases cytotoxic T cells (that can reduce viral load) and may be considered as a "therapeutic vaccine" approach to the treatment of HIV on an intermittent dosage schedule. These sustained results are particularly surprising given the measured half-life of Met-enkelphalin in plasma is approximately two minutes.

CD3, CD4, and CD8 Cells

Patients treated with methionine enkephalin one month earlier were found to have sustained increases of T cells compared to baseline (mean CD3+180, CD4+37, CD8+128). In sharp contrast patients infused with n-saline one month earlier were found to have sharp declines in T cell numbers compared to baseline values (CD3−284, CD4−79−246).

CD56 Cells

Natural killer cells numbers were greater than baseline for both the met-enkephalin and n-saline infusion groups compared to baseline. However, the met-enkephalin group was significantly higher than the n-saline group (80+18 versus 137+21 p=0.03).

CD25 Cells (IL2 Receptor)

Interleukin II receptor expression was increased in both groups compared to baseline although the met-enkephalin had a larger increase than the n-saline group (45 versus 87 cells).

CD38 Cells

Both groups were found to have increases of CD 38 cell numbers above baseline (285 for the saline group versus 316 for the enkephalin group).

This study supports the hypothesis proposed by Walker and coworkers, that the most important cells in maintaining the immune system in AIDS patients are the cytotoxic T cells (CD3, CD8) (Walker, et al., *Nature*, 1987; 328: 345-348). These cytotoxic T cells are the same cells activated by vaccines (Belyakov, et al., *J. Clin. Invest.*, 1998; 102(112): 2072-2081). CD4 subsets also have cytotoxic actions against HIV (Hahn, et al., *Int. Rev. Immunol.*, 1999; 18(5-6): 449-464). NK cells also are cytotoxic against HIV (Melder, et al., *FASEB J.*, 1989; 3: 4).

In the present study CD56 cells were elevated in both enkephalin and saline treated groups (8-12 weeks of infusions). The significantly greater increase in the enkephalin group can be attributed to the activating effects of the enkephalin and resultant increases in the enkephalin group can be attributed on the NK cells. Saline infusions for 8-12 weeks may also activate the same systems to some extent due to the stress of the procedure resulting in some increase of the cytokines and CD25.

EXAMPLE 2

In vivo Administration of Met-Enkephalin of Advanced AIDS Patients

Six advanced AIDS patients with CD4 Counts of less than 200 cells per μl were treated with an intermittent therapy of met-enkephalin. During an initial dosage regimen, dosages of met-enkephalin were given at 20 μg/Kg bodyweight of the subject three times per week for 4 weeks. Thereafter, subjects were given 20-100 μg/Kg bodyweight on an as-needed basis. Patients 4 and 6 had intermittent treatments after an initial dosage regimen.

Results at the start of the regimen, after one month of regular initial dosage regimen, and, for patients 4 and 6, after 3 additional months of intermittent therapy are given in Table IV and V.

TABLE IV

AIDS Patients Rx Regimen and Clinical Evaluation

| Patient Description | Pre-Rx status | Met-Enk Rx Regimen | Treatment Duration | Associated Treatment | Clinical Evaluation |
|---|---|---|---|---|---|
| 1. 42 Yr. male Homosexual | Kapos Sarcoma (Cutaneous) Pneumocystis carinii AIDS - (IV, C,.D) | 20 μg/Kg, 3x/wk (May 15, 1987) AZT (May 1987) | 4 mos. | | Kaposi Sarcoma stable No opportunistic infection |
| 2. 42 Yr. Male African | Pheumocystis Carinii, Esophageal Candidiasis; Cerebral Toxoplasmosis; Generalized is Cryptococcus (lung, G.I Bone Marrow Meningitis, Pericarditis) Kaposi Sarcoma stable AIDS - (IV, C, D) | 20 μg/Kg 3x wk (December 1985); to 100 μg/Kg 3x/wk (October 1987) | 10 mos. | Amphotericin Sulfadizine Vincristine Miconazol | No opportunistic infection except candida esophagitis Shigella enteritis cured Kaposi sarcoma stable Klebsiella septicemia cured |
| 3. 34 Yr. Male Homosexual | Kaposi Sarcoma (cutaneous lymph nodes) AIDS - (IV, C, D) | 20 μg/Kg, 3x wk (October 1985); to 100 μg/Kg; 3x (October 1987) | 24 mos. | Local Liquid N2 | Kaposi sarcoma stable (some remission, some new lesions) No opportunistic infections Salmonella septicemia at month 22 |
| 4. 37 Yr. Female African | Cerebral Toxoplasmosis; Candida Esophagitis (cutaneous) Kaposi Sarcoma AIDS (IV, C) | 20 μg/Kg, 3x wk/(January 1987) to 100 μg/Kg (February 1987) | 8 mos. | Sulfadiazine Pyrimethamine | Month 7 of RX Paraplegia and Sphincteral problems (HIV radiculitis?) Death of unknown origin (Bacterial infection? Lung emboli?) No recurrence of opportunistic infection |
| 5. 34 yr-Male Homosexual | Cerebral Toxoplasmosis AIDS (IV, C) | 20 μg Kg),3x/wk (January 2007) to 50 μg/Kg 3x/1 wk(March 1987) | 4 mos. (dropped out) | Sulfadiazine Pyrimethamine | Signs of cerebral atrophy after 2 mos. of RX HIV dementia No recurrence of opportunistic infection |
| 6. 31 Yr. Male Homosexual | Non Hodgkin Lymphoma Cerebral Toxoplasmosis Mycobacterium Kansani Kaposi Sarcoma (Cutaneous) AIDS - (IV, C, D) | 20 μg/Kg. 3x/wk (April 1986) to 100 μg/Kg (May 1987) | 11 mos. (dropped out) | | Disappearance of skin lesions at first (biopsy) but relapse (7 months) with probable lung involvement at month 11 No recurrence of opportunistic infection. |

TABLE V

AIDS Patients Immunology

| Patient # | Start | 1 Month | 4 Months | Other Readings (Months) | Other Readings (Months) |
|---|---|---|---|---|---|
| Lymphocytes/mm$^3$ | | | | | |
| 1 | 578 | — | 1130* | | |
| 2 | 700 | 1066* | 1172* | 540(8 M) | 360(10 M) |
| 3 | 1716 | 2080* | 1776* | 1173(24 M) | |
| 4 | 1380 | 1440* | 1620* | 969(7 M) | |
| 5 | 896 | 928* | 360 | — | |
| 6 | 247 | 324* | 252 | 112(11 M) | |
| CD3/mm$^3$ | | | | | |
| 1 | 387 | — | 881* | — | |
| 2 | 616 | 820 | 1337 | 410(8 M) | 256(10 M) |
| 3 | 1287 | 1560* | 1598* | 961(24 M) | |
| 4 | 730 | 940* | 790* | 532(7 M) | |
| 5 | 689 | 677 | — | — | |
| 6 | 205 | 250* | 164 | 78(11 M) | |
| CD4/mm$^3$ | | | | | |
| 1 | 29 | 68* | — | — | |
| 2 | 28 | 43* | 49* | 32(8 M) | 7(10 M) |
| 3 | 205 | 437* | 391* | 106(24 M) | |
| 4 | 40 | 40 | 60* | 58*(7 M) | |
| 5 | 63 | 65* | 50 | — | |
| 6 | 25 | 32* | 13 | 10(11 M) | |

TABLE V-continued

AIDS Patients Immunology

| Patient # | Start | 1 Month | 4 Months | Other Readings (Months) | Other Readings (Months) |
|---|---|---|---|---|---|
| CD8/mm³ | | | | | |
| 1 | 61 | — | 66* | — | |
| 2 | 546 | 767* | 1271* | 340(8 M) | 23(10 M) |
| 3 | 1047 | 1144* | 1154* | 821(24 M) | |
| 4 | 650 | 860* | 770* | 610(7 M) | |
| 5 | 609 | 594 | 198 | — | |
| 6 | 205 | 250* | 164 | 78(11 M) | |
| Ratio CD4/CD8 | | | | | |
| 1 | 0.5 | — | 1.0* | — | |
| 2 | 0.05 | 0.06* | 0.40 | 0.09*(8 M) | 0.02(10 M) |
| 3 | 0.02 | 0.38* | 0.34* | 0.13(24 M) | |
| 4 | 0.06 | 0.05 | 0.08* | 0.09*(7 M) | |
| 5 | 0.10 | 0.11* | 0.26* | — | |
| 6 | 0.10 | 0.13* | 0.08 | 0.13*(11 M) | |
| PHA (cpm × 10³) | | | | | |
| 1 | 213 | — | — | — | |
| 2 | 42 | 8 | 28 | 15(8 M) | 11(10 M) |
| 3 | 144 | 72 | 128 | 227*(24 M) | |
| 4 | 92 | 151* | 187* | 16(7 M) | |
| 5 | 48 | 82* | 60* | — | |
| 6 | 96 | 86 | 37 | 8(11 M) | |
| PWM (cpm × 10³) | | | | | |
| 1 | 32 | — | — | — | |
| 2 | 14 | 6 | 7 | 12(8) | 9(10 M) |
| 3 | 14 | 19* | 12 | 57*(24 M) | |
| 4 | 21 | 25* | 47* | –(7 M) | |
| 5 | 13 | 18* | 12 | — | |
| 6 | 17 | 19* | — | — | |
| NK(%) | | | | | |
| 1 | 3 | — | 17* | — | |
| 2 | 27 | 27 | 6 | — | |
| 3 | 26 | 43* | 33* | 13(8 M) | |
| 4 | 5 | 5 | 4 | 30*(24 M) | |
| 5 | 2 | 7* | — | 16*(7 M) | |
| 6 | 18 | 19* | — | –(11 M) | |
| IL2 (Units) | | | | | |
| 1 | 0.04 | — | 0.1* | — | |
| 2 | 0 | — | — | 0.1*(8 M) | 0(10 M) |
| 3 | 0.34 | 0.43* | 0 | — | |
| 4 | 0 | 0 | 0 | 0.03* | (7 M) |
| 5 | 0 | 0 | 0.03* | — | |
| 6 | 0.1 | 0 | — | –(11 M) | |

*Increase over baseline

Summary of Results:

The study described in this Example 2 demonstrates that intermittent dosage schedules provided comparable or better results in some patients to patients with continued regimens comparable to the initial dosage regimen. In particular, patients 4 and 6 showed positive results over an extended time period, with no recurrence of opportunistic infection. Patient 6 had a disappearance of skin lesions for an extended period of time. Changes included a visible reduction in size in some tumors, as well as tumor color resolution to white.

Patient 4 demonstrated increased lymphocyte, CD3, CD4, and CD8 counts; Patient 6 experienced increased lymphocyte counts compared to baseline. The principal immunological effects were increases in T cell subsets (CD3, CD4 and CD8) and blastogenesis with activation of gene transcription.

Thus, this clinical data demonstrates that an intermittent dose therapy of met-enkephalin can increase gene transcription of T cells in advanced AIDS patients and reduce or stabilize Kaposis sarcoma nodules.

It will be recognized by those of skill in the art that the active agents and methods of the present invention may be further modified without departing from the spirit and scope of the invention, and are not limited by the foregoing examples or preferred embodiments. This disclosure is intended to cover all variations, uses, or adaptations of the invention that generally follow the principles of the invention in the art to which it pertains.

I claim:

1. A method of treatment of an immunocompromised patient, which method comprises:

(a) administering an enkephalin peptide comprising SEQ ID NO: 1, either alone or in conjunction with other therapies, in an initial dosage regimen, wherein each dose in the regimen is 1 to 250 µg/Kg bodyweight of the patient, said initial dosage regimen inducing an immune system response in the patient, (b) discontinuing said initial dosage regimen with no further administration of said enkephalin peptide for a period of 4 to 24 weeks, wherein the immune system response is sustained during said period in which said administration of said enkephalin peptide is discontinued, and wherein said sustained immune system response comprises an elevated amount of at least one selected from the group consisting of cytotoxic T cells, natural killer cells, CD38 cells and interleukin II receptor expression in comparison to a baseline value, (c) administering booster dosages of said enkephalin peptide thereafter as necessary to maintain the sustained immune system response.

2. The method of claim 1, wherein the dosage of enkephalin peptide during the initial dosage regimen is 20 μg/Kg bodyweight of the patient.

3. The method of claim 1, wherein the need for periodic booster shots is determined by measuring the patient's sustained immune response from 4 to 16 weeks after cessation of the initial dosage regimen, and comparing the sustained immune response with both the baseline value and a response value measured at the end of the dosing schedule.

4. The method of claim 1, wherein periodic booster dosages are given, as needed, up to 5 times a week for 1 to 4 weeks.

5. The method of claim 1, wherein the booster dosage of enkephalin peptide after the initial dosage regimen ranges from 20 to 100 μg/Kg bodyweight.

6. The method of claim 1, wherein the initial dosage regimen is 1-5 times per week over a 4-12 week period.

7. The method of treatment of claim 1, wherein the other therapies include cytokine, antiviral, antibiotics, antifungal, antiparasite and anti-tumor therapies.

8. The method of claim 1, wherein said initial dosage regime is once per week for 4 to 12 weeks.

* * * * *